United States Patent [19]

Milani et al.

[11] 3,946,743
[45] Mar. 30, 1976

[54] DEFIBRILLATING ELECTRODE

[75] Inventors: Dean L. Milani, Highland Park; Richard G. Kerwin, Prospect Heights, both of Ill.

[73] Assignee: Medical Research Laboratories, Inc., Park Ridge, Ill.

[22] Filed: Jan. 6, 1972

[21] Appl. No.: 215,727

[52] U.S. Cl. ............... 128/404; 128/419 D
[51] Int. Cl.² ............................ A61N 1/04
[58] Field of Search ....... 128/419 D, 404, 405, 406, 128/416, 417, 418, 419 R, 420, 421, 422, 423, 424, 2.1 E, 2.06 E; 116/121

[56] References Cited
UNITED STATES PATENTS

| | | |
|---|---|---|
| 2,447,127 | 8/1948 | Landauer .......................... 128/405 |
| 3,093,136 | 6/1963 | Lohr ............................... 128/419 D |
| 3,196,877 | 7/1965 | Corbin ............................ 128/419 D |
| 3,224,447 | 12/1965 | Becker et al. ................... 128/419 D |
| 3,605,754 | 9/1971 | Jaros et al. ..................... 128/419 D |
| 3,625,222 | 12/1971 | Shihizu ............................ 128/405 |

*Primary Examiner*—Robert W. Michell
*Assistant Examiner*—Lee S. Cohen
*Attorney, Agent, or Firm*—Robert M. Wolters

[57] ABSTRACT

Electronic defibrillating mechanism in which the electrodes comprise handles to be grasped by an operator with electrodes in the form of discs to be placed against the chest of the patient. The handles are provided with push buttons, and a neon ready-light is provided in each push button to indicate when the apparatus is charged to the desired extent for the operator to effect a defibrillating discharge.

3 Claims, 4 Drawing Figures

DEFIBRILLATING ELECTRODE

BACKGROUND OF THE INVENTION

Electronic defibrillating apparatus are well known in the art. It is recognized that when the heart of a person goes into fibrillation, a discharge of a predetermined amount of electrical energy into the chest of the patient may stop the fibrillation. In accordance with conventional practice electrodes are provided which are placed on the chest of the patient. A capacitor in the apparatus is charged until a predetermined number of watt-seconds of energy is stored. A meter on the apparatus indicates when this predetermined quantity of electrical energy has been stored, and the doctor or technician may then close a switch to discharge the capacitor into the body of the patient whereby, hopefully, to stop fibrillation of the heart. Additional charges subsequently may be discharged into the body of the patient if the first discharge does not stop fibrillation. Such an electric discharge can have other beneficial effects on a patient, such as restarting a heart which has stopped for one reason or another.

In all previous defibrillating apparatus with which we are familiar it has been necessary for the doctor or technician to observe a meter on the apparatus to determine when the capacitor has charged to the requisite extent. Thus, the doctor or technician must monitor the apparatus, while at the same time watching the patient for various medical signs, and simultaneously properly positioning the electrodes on the chest of the patient.

SUMMARY AND OBJECTS

In accordance with the present invention it is an object to provide defibrillating apparatus in which indicating means is provided on the electrodes for indicating when the capacitor has been charged to the proper extent.

More particularly, it is an object to provide defibrillating electrodes having neon indicator lamps thereon which glow when the capacitor has reached the proper level.

In accordance with the present invention electrodes are provided with handles to be grasped by the hands of the operator, there being provided push buttons which are lighted by the neon ready-light on the handles, whereby the operator need not visually monitor the defibrillating apparatus, but can watch the patient and cannot miss seeing the neon ready-lights come on. There may be neon ready-lights on each of a pair of electrodes, with push button switches in each electrode handle. However, it is contemplated by the present invention that there might be only one push button switch, with both handles having neon ready-lights, or with there being only a neon ready-light in the push button on the handle having the switch.

It is further within the contemplation of the present invention to use snap-in electrodes so that different sizes might be used for adults and for children.

DESCRIPTION OF THE DRAWINGS AND DETAILED SPECIFICATION

The present invention will be understood best with reference to the following drawings when taken in connection with the accompanying specification, wherein.

Figure 1:
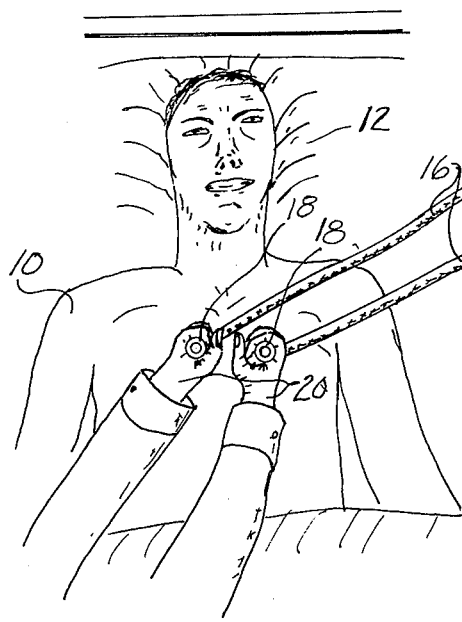
FIG. 1 is a plan, somewhat schematic view of apparatus constructed in accordance with the present invention.

Turning now in greater particularity to the drawings, a patient 10 is seen lying on a suitable support 12 which may be a bed, cot, stretcher, etc. Defibrillating apparatus is illustrated at 14, and will be understood to be generally conventional in nature, including a rectifier circuit for converting alternating current energy from an outlet to direct current of suitable voltage for charging a capacitor in the apparatus. Other types of power supplies might be used for portable equipment, and all of this is known to those skilled in the art. Flexible leads 16 extend from the apparatus 14 to electrodes 18 held in the hands 20 of an operator, such as a doctor or technician, with the active elements of the electrodes pressed against the chest of the patient 10.

As will be apparent from FIG. 1, it is substantially impossible for the apparatus 14 to be close enough to the patient for the operator to observe both closely at the same time. Furthermore, defibrillation or restarting of a stopped heart must often be accomplished in the dark, or in a poorly lit location which makes visual observation of the defibrillating apparatus 14 difficult or impossible.

Figure 2:
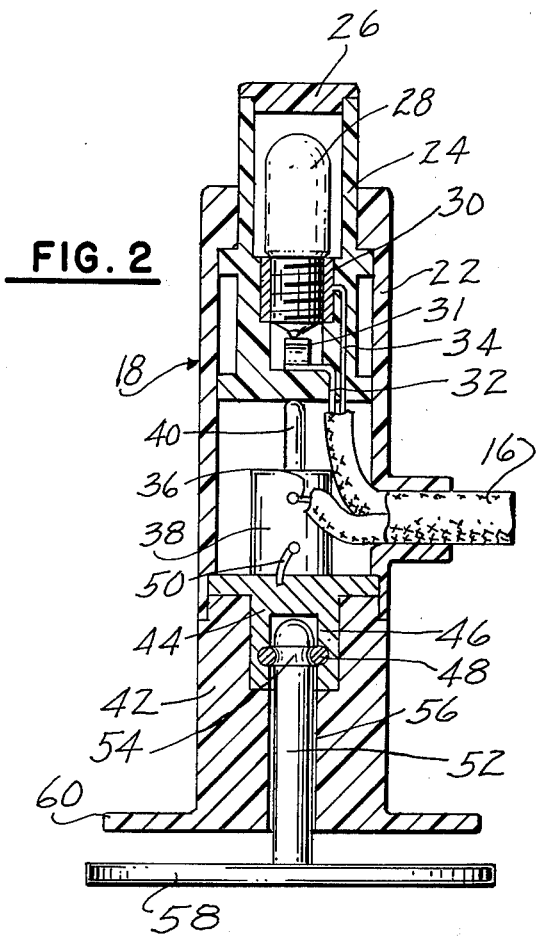
FIG. 2 is a longitudinal sectional view through the electrode of the present invention.

One of the electrodes 18 is shown in considerable detail in FIG. 2 and comprises a plastic or other insulating hollow handle 22 having a transparent or translucent push button 24 reciprocably mounted in the upper end thereof. The top portion of the push button 24 as indicated at 26 is removable, and a neon bulb 28 is suitably mounted within the push button, as by threading into a socket 30 with the center contact of the bulb engaging a center contact 31 mounted below the threaded socket. The center contact 31 is connected to a wire 32, while the socket 30 is connected to a wire 34, the wires 34 and 32 comprising a portion of one of the cables 16. As will be understood, the wires 32 and 34 are connected to the opposite sides of the capacitor which is charged in the apparatus 14.

Another wire 36 in the cable 16 leads to a switch 38 having a reciprocal plunger 40 which is spring urged upwardly, and which presses against the underside of the push button 26 for depression thereby.

A separable portion 42 of the electrode handle mounts a metal socket 44 having a center cylindrical opening 46 having a snap ring 48 therein. The handle portion 42 upon mounting the socket 44 may be cemented or fused in place and need not thereafterwards be separable. The socket 44 is connected by a wire 50 to the opposite side of the switch 38 from the wire 36.

A metallic stem 52 has an annular groove 54 therein, and is received in a bore 56 of the handle portion 42 and also in the bore 46 of the socket 44, the snap ring 48 snapping into the groove 54 to hold the stem 52 in place. A metallic electrode disc 58 is fixed to the outer end of the stem 52 and is spaced from an insulating disc 60 integral with the handle portion 42.

Figure 3:
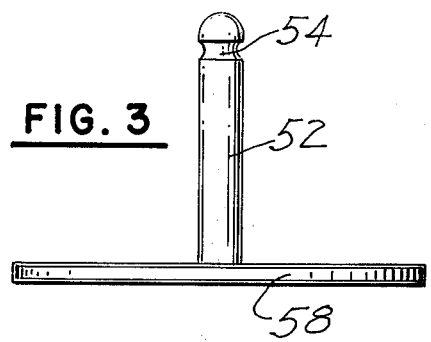
FIG. 3 is a side view of an adult size electrode.
Figure 4:
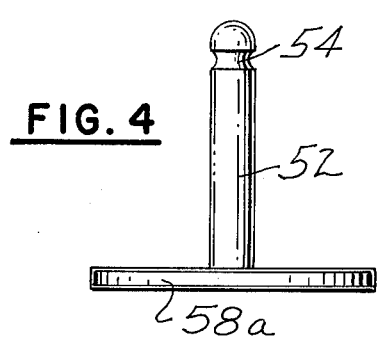
FIG. 4 is a similar side view of a child size electrode.

As may be seen by comparing FIGS. 3 and 4, the disc may be relatively large as indicated at 58 in FIG. 3, or it may be smaller as indicated at 58a in FIG. 4. The reason for this is that there are optimum positions on the chest of a patient for positioning of the electrode discs, and the larger discs as in FIG. 3 are most efficient for positioning on the chest of an adult whereas such discs could not be properly positioned on the chest of a child without contacting one another and shorting out the discharge. Thus, the larger disc and stem are snapped out of the handle and the smaller disc and stem are snapped in for use with a child.

As will now be understood, when the defibrillating apparatus 14 is turned on the capacitor will charge. When the desired charge level is reached, corresponding to a predetermined number of watt-seconds energy, the neon ready-lights 28 will both glow. Since they glow, they are readily seen by the operator, such as a doctor or technician who may be watching the patient's face for other vital signs. The operator then simply depresses both push buttons with his thumbs, providing the patient with the necessary direct current shock to stop fibrillation, or to restart a stopped heart, etc. It is not necessary for the operator to take his eyes from the face of the patient to see the lighted push buttons indicating where his thumb should be pushed. The push buttons are discernable to anyone in the area indicating that the capacitor is charged, and that everyone should keep his hands away except for the operator. Furthermore, the neon ready-lights are readily discernable in the dark, and may even help to locate the electrodes in a poorly lit area, such perhaps as in an ambulance, or in a combat field.

By having two duplicate electrodes, each with a push button, a certain safety factor is introduced in that both push buttons must be depressed. Synchronization of the depression is not important, but the second must be depressed before the first is released. Economies of manufacture may be obtained by utilizing only one switch, although it is preferable to retain both neon bulbs for location of the electrodes. Obviously, the neon bulb associated with the electrode which does not have a switch can also be eliminated for reasons of economy but this is undesirable as it detracts from the findability of the electrodes in a dark environment, and it detracts from the ability of the operator properly to position the electrodes on the chest without taking his eyes from the face of the patient.

The specific example of the invention as herein shown and described is for illustrative purposes. Various changes in structure will no doubt occur to those skilled in the art, and will be understood as forming a part of the present invention insofar as they fall within the spirit and scope of the appended claims.

The invention is claimed as follows:

1. Electrode structure for application to a body of a patient comprising a handle adapted to be grasped in the hand of an operator, an electric contact on said handle to be pressed against the body of a patient, a normally open electric switch carried by said handle and electrically connected to said contact, a switch-closing device on said handle adapted to be depressed by a finger of an operator and mechanically interconnected with said switch to close said switch upon depression of said switch-closing device, electric connection means connected to said switch and adapted to be connected to a source of electric power for connection of said source to said contact upon closure of said switch, and a ready-light carried by said handle in close proximity to said device illuminating said device when energized, said ready-light being electrically connected to said electric connection means and thus being energized when said source is in a ready condition, said switch-closing device comprising a push button and the light being mounted in said push button, said push button being at least in part pellucid and thus transmitting light.

2. An electrode structure as set forth in claim 1 wherein said contact comprises a plate.

3. An electrode structure as set forth in claim 2 and including means quickly detachably mounting said plate on said handle.

* * * * *